US012178957B2

(12) United States Patent
Lin et al.

(10) Patent No.: US 12,178,957 B2
(45) Date of Patent: Dec. 31, 2024

(54) LOCKING MECHANISM FOR AEROSOL DRUG DELIVERY DEVICE

(71) Applicant: MICROBASE TECHNOLOGY CORP., Taoyuan (TW)

(72) Inventors: Chih-Chieh Lin, Taoyuan (TW); Chiu-Ju Shen, Taoyuan (TW); Yi-Ting Lin, Taoyuan (TW); Jo-Ling Wu, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 1030 days.

(21) Appl. No.: 17/258,753

(22) PCT Filed: Nov. 8, 2019

(86) PCT No.: PCT/CN2019/116789
§ 371 (c)(1),
(2) Date: Jan. 8, 2021

(87) PCT Pub. No.: WO2020/098578
PCT Pub. Date: May 22, 2020

(65) Prior Publication Data
US 2021/0322685 A1    Oct. 21, 2021

(30) Foreign Application Priority Data
Nov. 16, 2018    (CN) .......................... 201811365373.3

(51) Int. Cl.
*A61M 15/00*    (2006.01)
(52) U.S. Cl.
CPC .............................. *A61M 15/0001* (2014.02)

(58) Field of Classification Search
CPC .......... A61M 11/00; A61M 11/006–02; A61M 11/06; A61M 11/08; A61M 15/00–0001; A61M 15/0065–0083; A61M 15/009
See application file for complete search history.

(56) References Cited

U.S. PATENT DOCUMENTS

2004/0094147 A1* 5/2004 Schyra .................... A61M 5/50
128/200.14
2022/0047823 A1* 2/2022 Säll ...................... B05B 11/1091

FOREIGN PATENT DOCUMENTS

CN            1678406 A       10/2005
CN         202211912 U         5/2012
(Continued)

OTHER PUBLICATIONS

International Search Report for PCT/CN2019/116789.

*Primary Examiner* — Rachel T Sippel

(57) ABSTRACT

A locking mechanism for an aerosol drug delivery device includes a first housing, a second housing, a screw and a fastening member. The first housing has a contact portion and a fastening space formed beside the contact portion. The second housing is rotatably connected with the first housing and is capable of rotating relative to the first housing along a rotation axis. The screw is rotatably connected with the second housing and is capable of rotating relative to the second housing along a central axis parallel to the rotation axis. The fastening member is movably connected with the screw and capable of being driven by the screw to move toward the contact portion. The fastening member includes a fastening portion capable of being displaced when contacting with the contact portion and entering into the fastening space to limit the relative rotation between the first housing and the second housing.

16 Claims, 12 Drawing Sheets

(56) References Cited

FOREIGN PATENT DOCUMENTS

| | | | |
|---|---|---|---|
| CN | 103446646 | A | 12/2013 |
| CN | 108495680 | A | 9/2018 |
| CN | 209347829 | U | 9/2019 |
| WO | 2008015542 | A1 | 2/2008 |

\* cited by examiner

LOCKING MECHANISM FOR AEROSOL DRUG DELIVERY DEVICE

CROSS-REFERENCE TO RELATED APPLICATION

This application is the U.S. national phase of international application No. PCT/CN2019/116789 filed on Nov. 8, 2019, the entire contents of which are hereby incorporated by reference.

BACKGROUND OF THE INVENTION

1. Field of the Invention

The present invention relates to a locking mechanism and, in particular, to a locking mechanism for an aerosol drug delivery device.

2. Description of the Related Art

An aerosol drug delivery device is used by a patient to deliver drug in an aerosol form for a specific therapy purpose. For example, a portable vapor inhalation bottle for a person with asthma is a typical aerosol drug delivery device.

Due the uniqueness of the drug, it must be ensured that when the treatment is about to end (that is, the drug is consumed to a certain amount), a locking mechanism is also required to remind the user to replace the drug in time. One conventional locking mechanism uses the combination of a spring and a push rod. The spring is pre-pressed in the device, and the push rod approaches the pre-pressed spring every time the user uses the device. When the push rod touches the pre-pressed spring, the spring is triggered to be restored to its un-pressed state to lock the device.

Since the spring needs to be pre-pressed, a space in the housing of the device is required to accommodate the pre-pressed spring, and during the assembly process the spring and the space must be aligned precisely. This increases the costs and structural complexity. Furthermore, the pre-pressed spring may be accidentally triggered due to the drop of the device, which results in the false lock of the device.

BRIEF SUMMARY OF THE INVENTION

A locking mechanism for an aerosol drug delivery device includes a first housing, a second housing, a screw and a fastening member. The first housing has at least one contact portion and at least one fastening space formed beside the contact portion. The second housing is rotatably connected with the first housing and is capable of rotating relative to the first housing along a rotation axis. The screw is rotatably connected with the second housing and is capable of rotating relative to the second housing along a central axis parallel to the rotation axis. The fastening member is movably connected with the screw and is capable of being driven by the screw to move toward the contact portion. The fastening member includes a fastening portion capable of being displaced when contacting with the contact portion and entering into the fastening space to limit the relative rotation between the first housing and the second housing.

In one embodiment, under an initial state the fastening member is located at one end of the screw away from the first housing.

In one embodiment, the locking mechanism may further include a projection disposed at the first housing. The position of the projection corresponds to one end of the screw, and the projection contacts with the screw when the first housing rotates relative to the second housing to drive the screw to rotate along the central axis.

In one embodiment, the screw may have a driven portion projected radially at the end contacting the projection for being driven by the projection.

In one embodiment, the fastening member may include a connecting portion and a connecting arm. The connecting portion has a screw hole for engaging with the screw, and the connecting arm has one end connected with the connection portion and another end being the fastening portion.

In one embodiment, the connecting portion and the connecting arm may be integrally formed. In another embodiment, the connecting arm may be a metallic spring plate and is inserted into the connecting portion.

In one embodiment, the fastening space may be a fastening groove formed at the inner surface of the first housing. In another embodiment, the fastening space may be formed at the outside of the first housing, and the locking mechanism further includes a block disposed at the outer surface of the second housing so that the fastening member is between the block and the fastening space when the fastening portion is limited in the fastening space.

In one embodiment, when under an initial state, the distance between the fastening portion and the rotation axis is larger than the distance between the outer surface of the second housing and the rotation axis.

In one embodiment, the central angle between the two ends of the fastening space is equal to or smaller than 25 degrees.

When using the locking mechanism for the aerosol drug delivery device, the second housing is rotated relative to the first housing to rotate the screw along the central axis to drive the fastening member to move toward the contact portion. Then the second housing is further rotated relative to the first housing to make the fastening portion be displaced when contacting with the contact portion and then enter into the fastening space to limit the relative rotation between the first housing and the second housing.

In one embodiment, in the first rotating step the fastening member is moved from an initial state located at one end of the screw away from the first housing.

In one embodiment, in the second rotating step the fastening portion restored to enter into the fastening space after being displaced by the contact portion.

DETAILED DESCRIPTION OF THE INVENTIONS

To facilitate understanding of the object, characteristics and effects of this present disclosure, embodiments together with the attached drawings for the detailed description of the present disclosure are provided.

Figure 1:
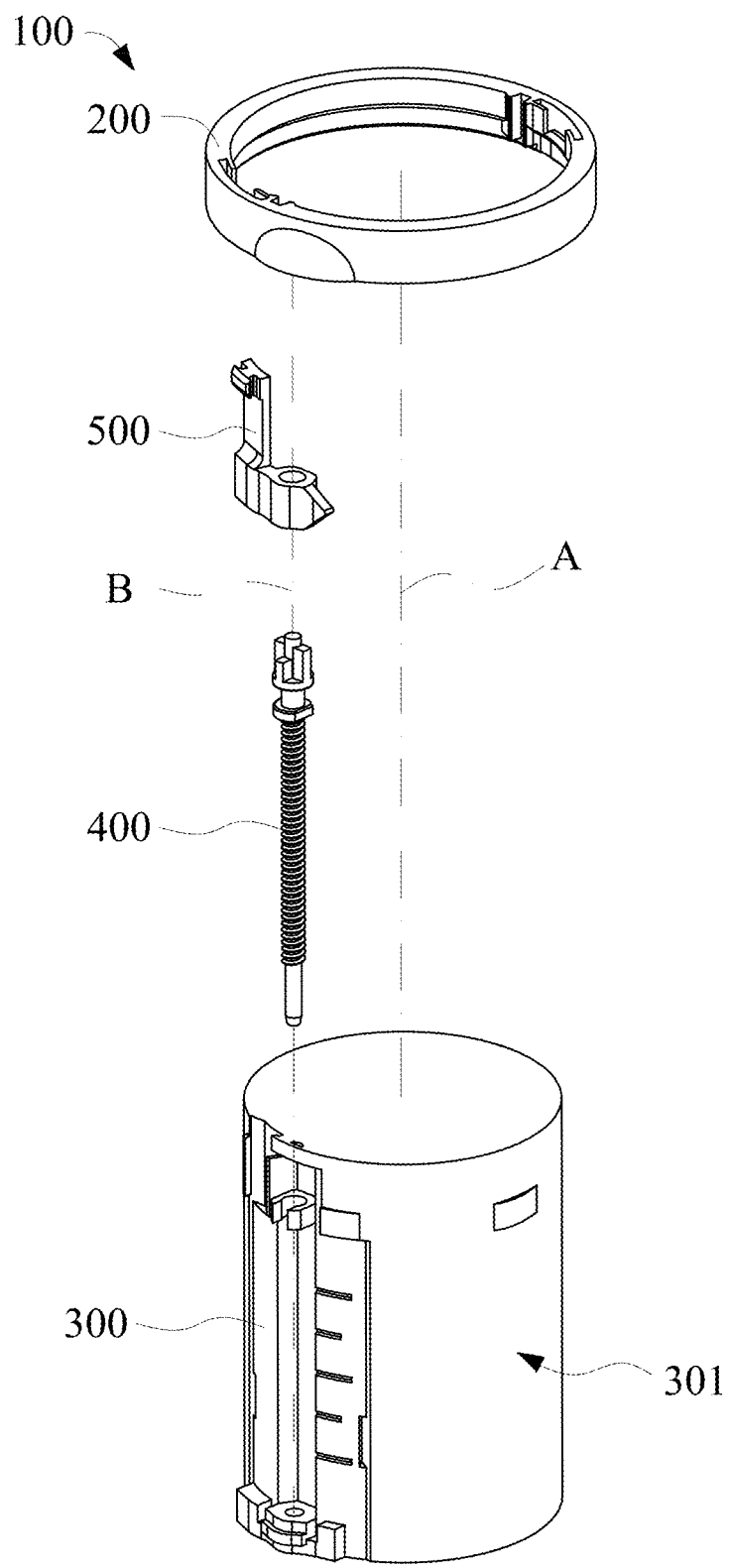
FIG. 1 is an exploded diagram showing the locking mechanism of the aerosol drug delivery device according to one embodiment of the invention.

Referring to FIG. 1, the locking mechanism 100 of the aerosol drug delivery device according to one embodiment of the invention includes a first housing 200, a second housing 300, a screw 400 and a fastening member 500. The first housing 200 and the second housing 300 are rotatably connected so that they can rotate relative to each other along a rotation axis A. The screw 400 is rotatably disposed at one side of the second housing 300 (the outer side of the outer surface 301 of the second housing 300), and the central axis B of the screw 400 is parallel to the rotation axis A. When the second housing 300 rotates relative to the first housing 200, the screw 400 also rotates along the central axis B. The fastening member 500 is also disposed at one side of the second housing 300, and is connected with and driven by the screw 400. When the screw 400 rotates, the fastening member 500 does not rotate with the screw 400 due to the limitation of the outer surface of the second housing. Therefore, the fastening member 500 is driven by the screw 400 to move along the screw 400.

Figure 2A:
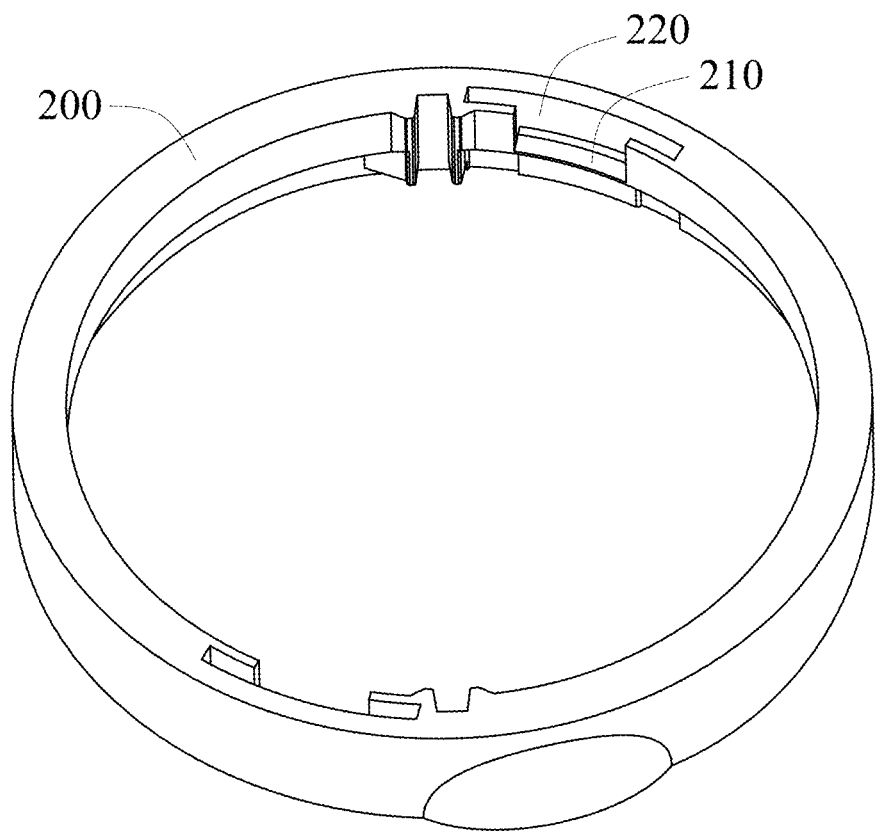
FIG. 2A is a schematic diagram showing the first housing of the locking mechanism of the aerosol drug delivery device shown in FIG. 1.
Figure 2B:
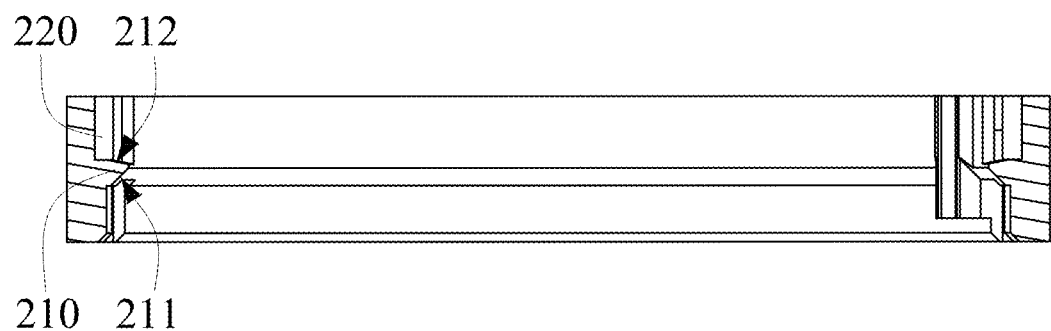
FIG. 2B is a sectional view of the first housing of the locking mechanism of the aerosol drug delivery device shown in FIG. 1.

Referring to FIGS. 2A and 2B, the first housing 200 has two contact portions 210 and two fastening spaces 220. Each fastening space 220 is a fastening groove formed at the inner surface of the first housing 200 and beside the contact portion 210. As shown in FIG. 2B, the two sides of the contact portions are the contacting side 211 and the position-limiting side 212, respectively, and the fastening space 220 is formed at the position-limiting side 212. The two sets of contact portions 210 and the fastening spaces 220 are formed in symmetry with respect to the rotation axis A. While in the present embodiment two sets of the contact portion 210 and the fastening space 220 are formed, in other embodiments the number of the contact portion 210 and the fastening space 220 may be different, and the way the contact portion 210 and the fastening space 220 are formed may also be different in view of different practical design requirements.

Figure 3A:
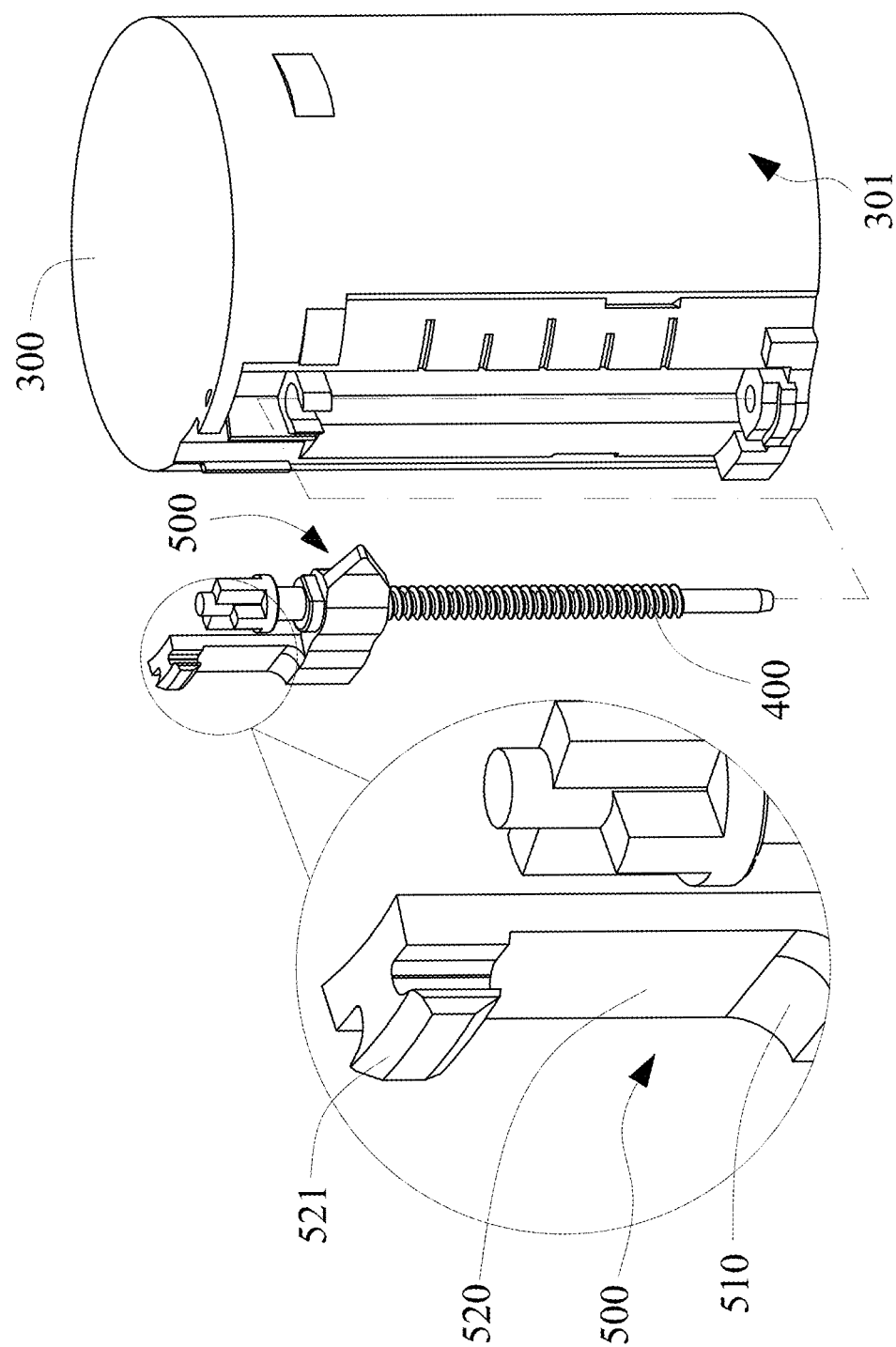
FIG. 3A is a partial enlarged view of the fastening member of the locking mechanism of the aerosol drug delivery device shown in FIG. 1.

Referring to FIGS. 2A, 2B and 3A, the fastening member 500 is connected with the screw 400 to move linearly along the screw 400. The fastening member 500 has a connecting portion 510 and a connecting arm 520. The connecting portion 510 has a screw hole 511 suitable for engaging with the screw 400, so that the connecting portion 510 can be driven by the screw 400 to move linearly on the screw 400 relative to the second housing 300. One end of the connecting arm 520 is disposed at the connecting portion 510. In the present embodiment, the connecting arm 520 has an elongated flat shape and extends from the connecting portion 510 toward the contact portion 210. Another end of the connecting arm 520 has a fastening portion 521 that is capable of being engaged within the fastening space 220. The fastening portion 521 is substantially in a frustum shape that is capable of slidably fitting into the fastening spaces 220, and a narrower neck portion is provided to connect the frustum with the connecting arm 520. The connecting portion 510, the connecting arm 520 and the fastening portion 521 of the fastening member 500 may be integrally formed. Alternatively, the connecting portion 510, the connecting arm 520 and the fastening portion 521 may be separate parts and are fixedly combined together to form the fastening member 500.

Figure 3B:
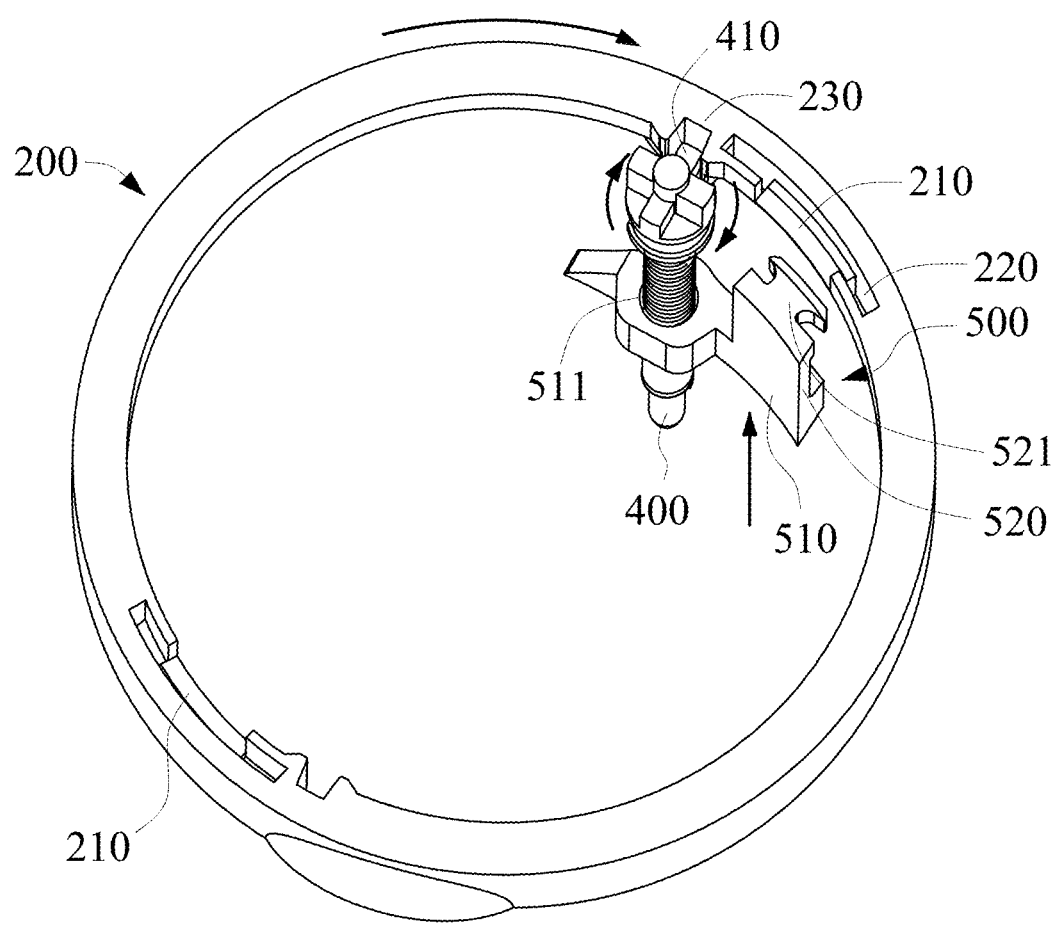
FIG. 3B is a schematic diagram showing the operation of the screw of the locking mechanism of the aerosol drug delivery device shown in FIG. 1.

Referring to FIG. 3B, two projections 230 are disposed at the inner surface of the first housing 200. The positions of the projections 230 correspond to one end of the screw 400 having a plurality of driven portions 410. As shown in FIG. 3B, the driven portions 410 are projected radially from the screw 400, and the shape of the projections 230 is designed to be capable of driving of the driven portions 410, so that when the first housing 200 rotates relative to the second housing 300, the projections 230 contact with the driven portions 410 and pushes the driven portions along the tangential direction to drive the screw 400 to rotate. In other embodiments, the number of the projections 230 may be different in view of different practical application needs. For example, the number of the projections 230 may be more than three, and the projections 230 may be disposed at the first housing 200 with equal intervals.

Note that there are multiple ways for the screw 400 to drive the fastening member 500 to move linearly, and the projections 230 can also be implemented by different ways. The position of the fastening space 220 is also not limited to the inner surface of the first housing 200. For example, the fastening space 220 can be formed to penetrate the first housing 200. The descriptions above are merely for exemplary purpose.

Figure 3C:
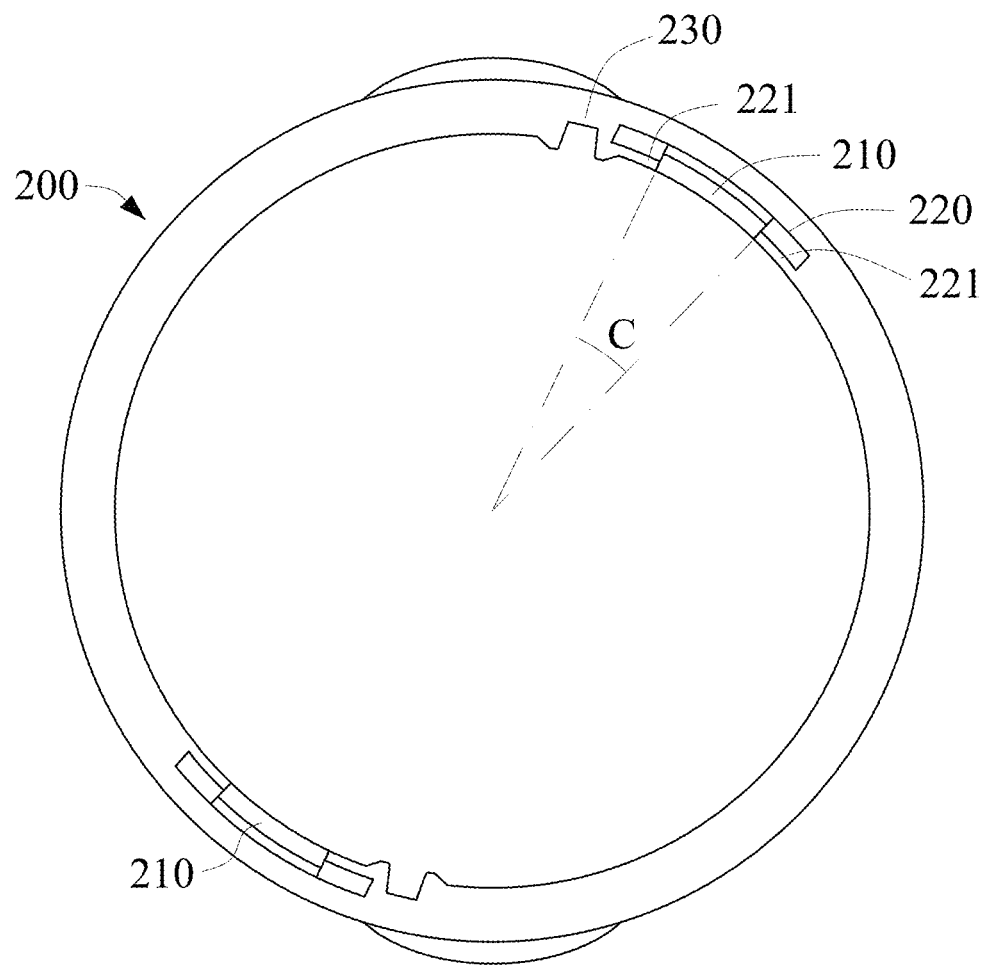
FIG. 3C is a schematic diagram showing the projection of the first housing of the locking mechanism of the aerosol drug delivery device shown in FIG. 1.

Referring to FIG. 3C, the second housing 300 rotates along the rotation axis A and the fastening member 500 is driven to move toward the fastening slot 220. Afterward, the fastening portion 521 contacts with the contact portion 210 and then further slides to pass the contact portion 210 and enter into the fastening slot 220. In the present embodiment, the fastening slot 220 may be a fastening groove have an arc shape as shown in FIG. 3C, and the central angle C between the two ends 221 of the fastening space 220 is preferably smaller than 25 degrees. Thus, when the fastening portion 521 reaches the contact portion 210, the width of the fastening space is wide enough for the fastening portion 521 to enter into the fastening space 220. After the fastening portion 521 enters into the fastening space 220, the fastening space 220 can also ensure that the fastening portion 521 is effectively limited within the fastening space 220 to limit the relative rotation between the first housing 200 and the second housing 300 to be within, for example, a small angle.

Figure 4A:
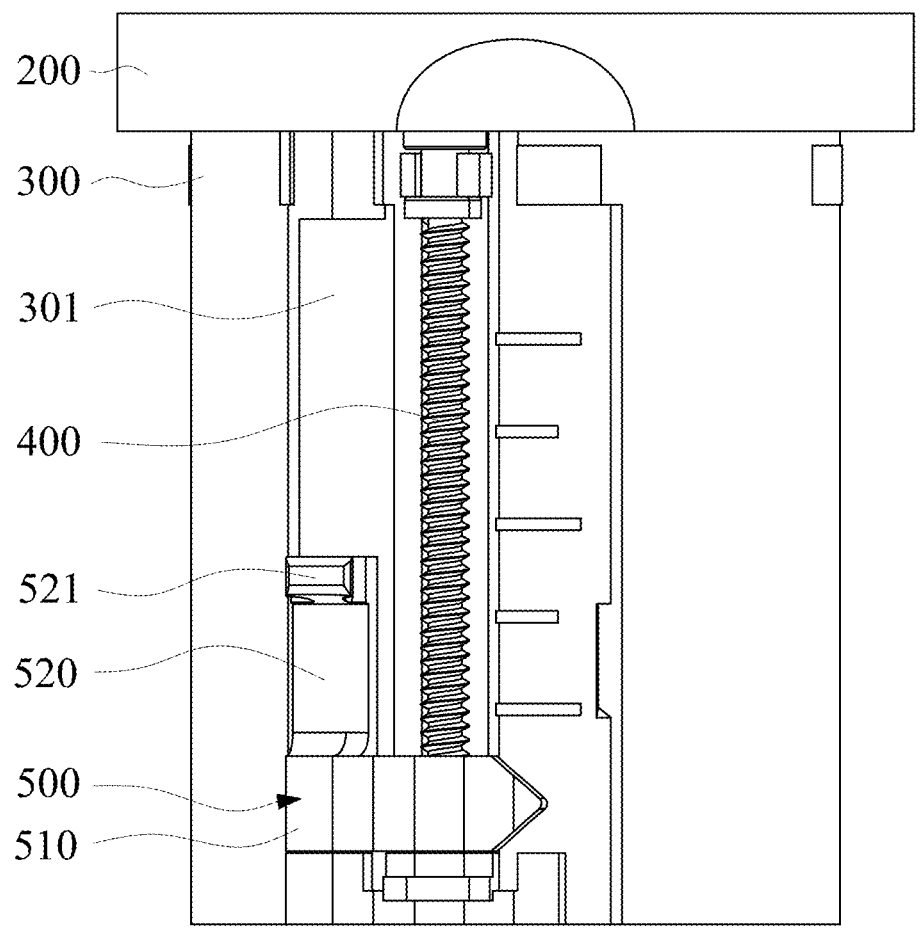
FIG. 4A is a schematic diagram showing the structure of the locking mechanism of the aerosol drug delivery device shown in FIG. 1.
Figure 4B:
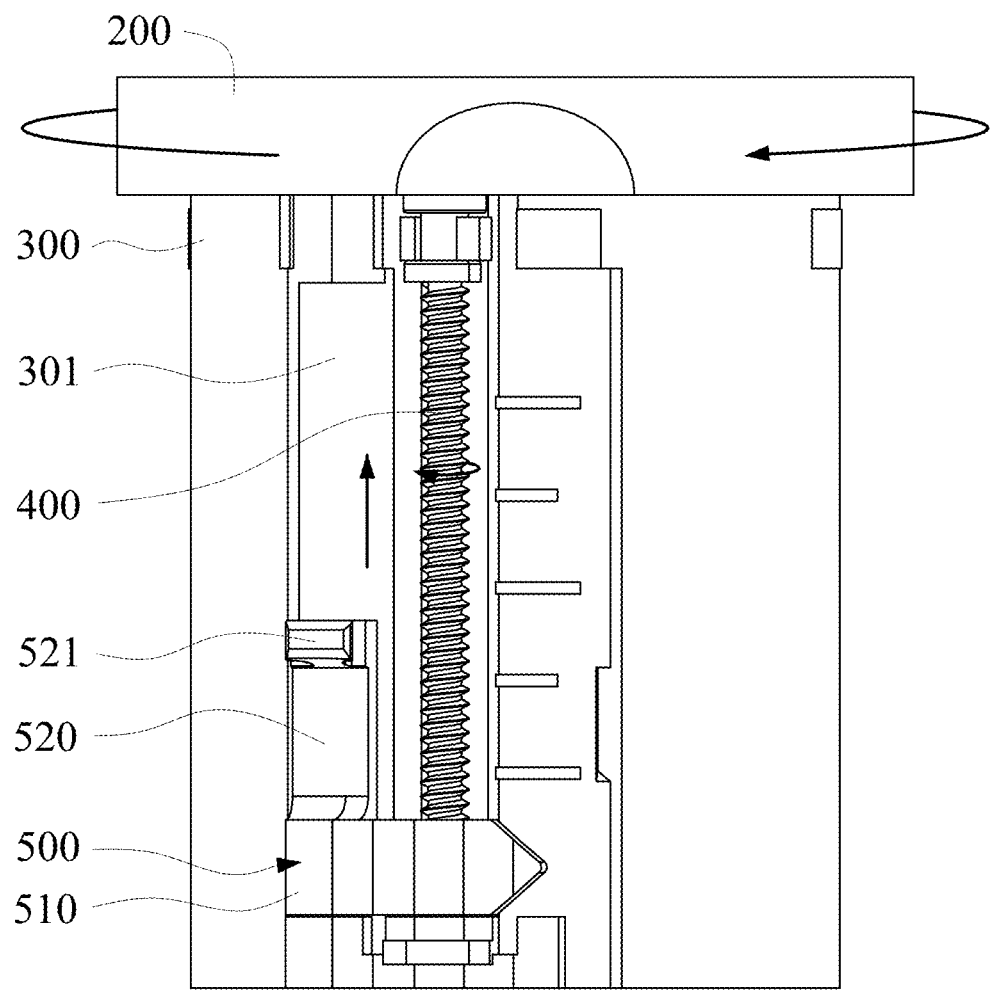
FIG. 4B is a schematic diagram showing the operation of the locking mechanism of the aerosol drug delivery device shown in FIG. 1.

FIGS. 4A and 4B are schematic diagrams shown the operations of the locking mechanism 100 of the aerosol drug delivery device of the present embodiment. Under the initial state shown in FIG. 4A, the fastening member 500 is at the bottom of the screw 400, that is, the end of screw 400 away from the first housing 200. When the first housing 200 rotates relative to the second housing, the fastening member 500, including its fastening portion 521, is driven by the screw 400 to move toward the contact portion 210 of the first housing 200.

Figure 5A:
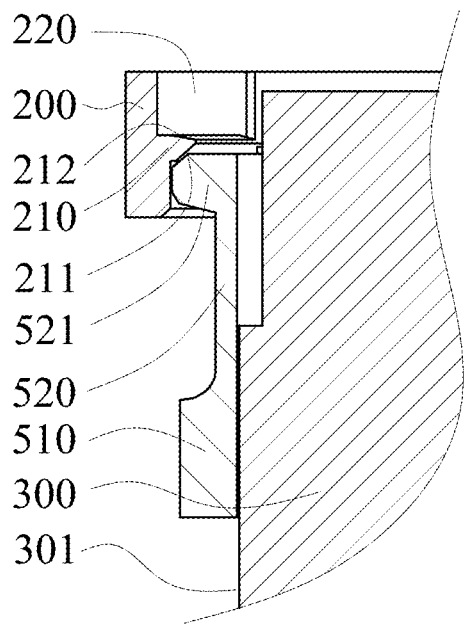
FIG. 5A is a partial sectional view showing the fastening portion of the locking mechanism of the aerosol drug delivery device shown in FIG. 1 contacts the contacting side.
Figure 5B:
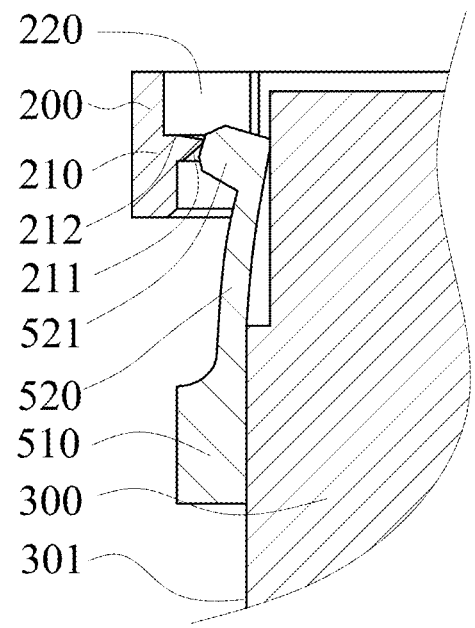
FIG. 5B is a partial sectional view showing the displacement of the fastening portion shown in FIG. 5A.

Please refer to FIGS. 5A to 5D. In FIG. 5A, when the second housing 300 keeps rotating relative to the first housing 200 so that the fastening member 500 moves to a preset position, the fastening portion 521 starts contacting with the contacting side 211 of the contact portion 210. As shown in FIG. 5B, when the fastening member 500 continues its movement toward the first housing 200, the fastening portion 521 is displaced. The connecting arm 520 is deformed temporarily due to the displacement of the fastening portion 521 until the fastening portion 521 passes the contact portion 210.

Figure 5C:
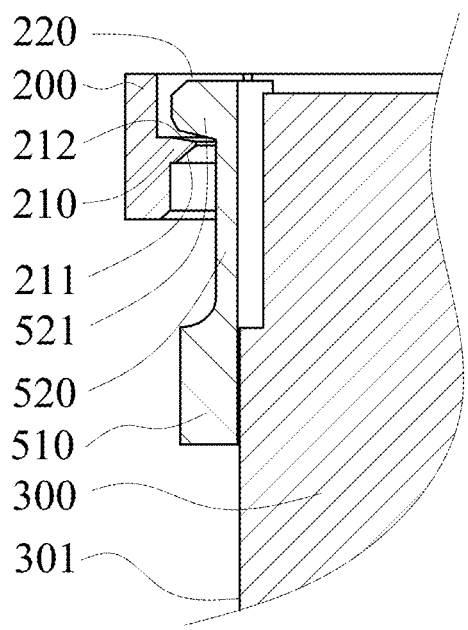
FIG. 5C is a partial sectional view showing that the fastening portion shown in FIG. 5A enters into the fastening space.

Referring to FIG. 5C, after the fastening portion 521 of the fastening member 500 passes the contact portion 210, the restoration force of the connecting arm 520 makes the fastening portion 521 slide to the position-limiting side 212 and further into the fastening space 220.

Figure 5D:
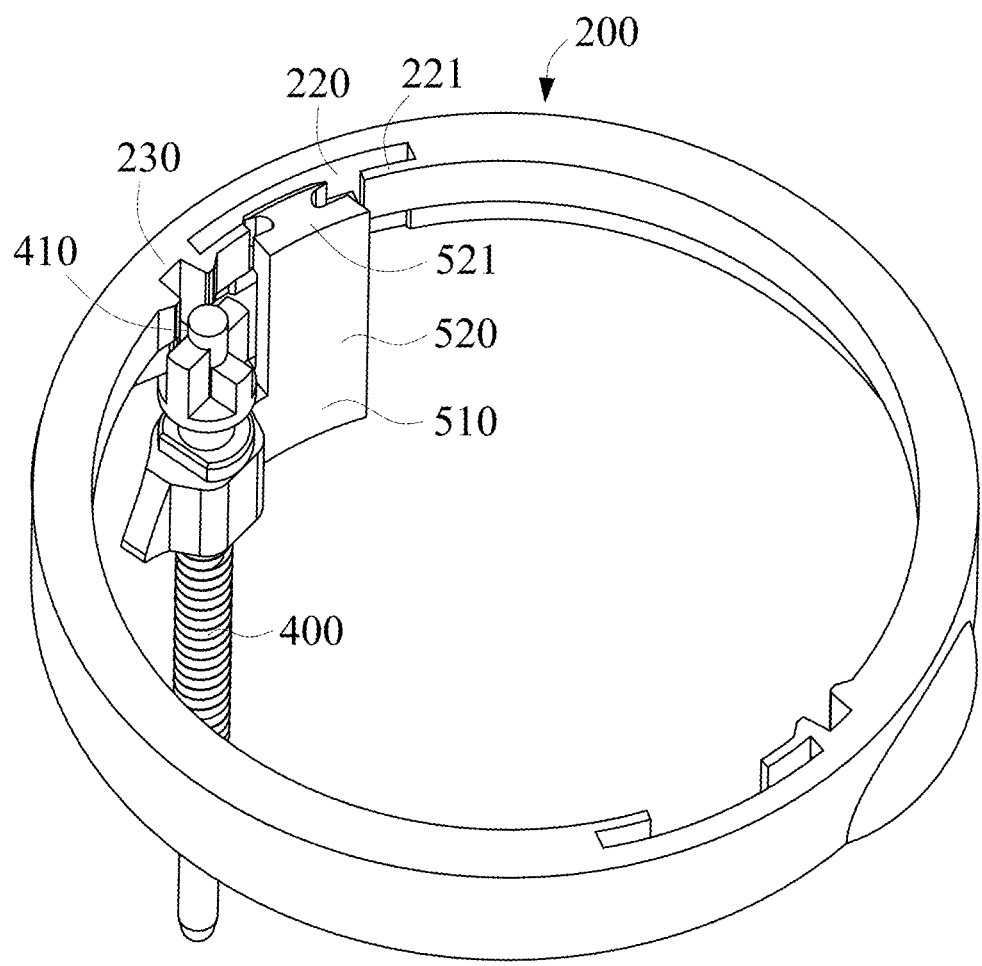
FIG. 5D is a schematic diagram showing that the fastening portion shown in FIG. 5A enters into the fastening space.

Referring to FIG. 5D, after the fastening portion 521 enters into the fastening space 220, the relative rotation between the first housing 200 and the second housing 300 is limited by the fastening portion 521 in the fastening space 220. The second housing 300 cannot freely rotate relative to the first housing 200 due to the limitation of the movement of the fasting portion 521 caused by the two ends of the fastening space 220. Therefore, the locking effect of the aerosol drug delivery device is achieved.

Figure 6:
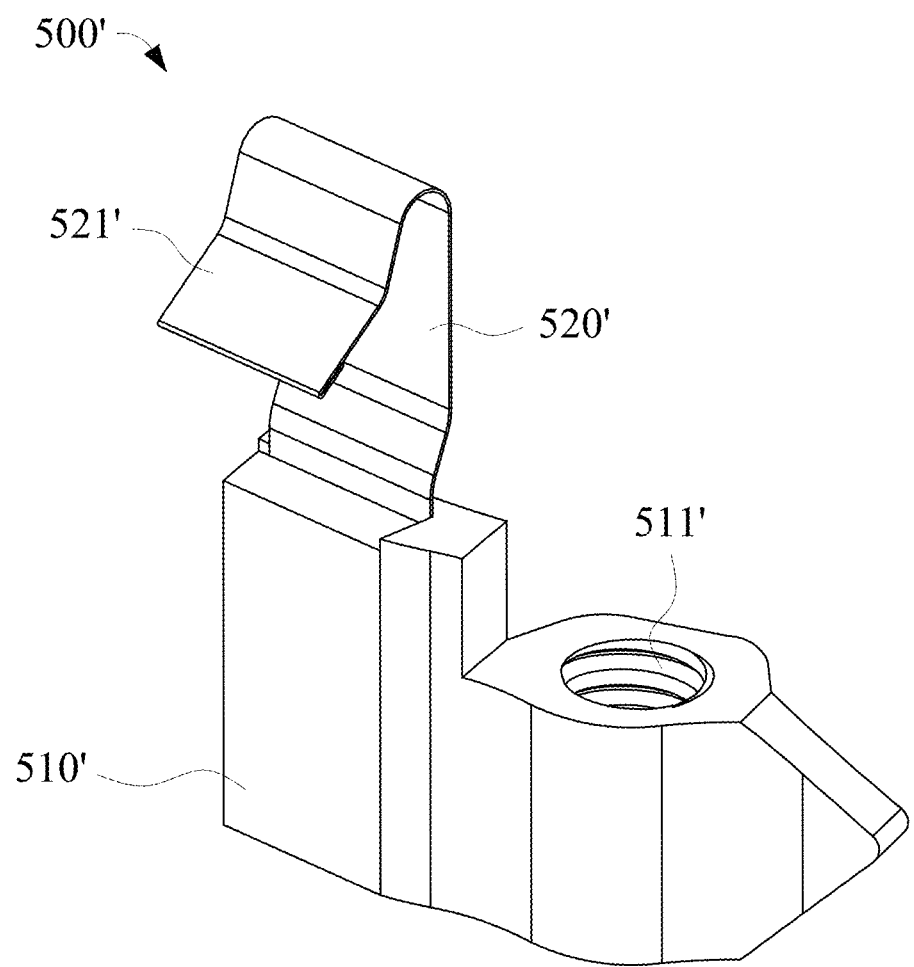
FIG. 6 is a schematic diagram showing another fastening member according to another embodiment of the invention.

Referring to FIG. 6, which shows another fastening member 500' of the locking mechanism 100 of the aerosol drug delivery device according to another embodiment of the invention. The fastening member 500' can selectively replace the fastening member 500 described above. Similar to the fastening member 500, the fastening member 500' is connected with the screw 400, and is driven by the screw 400 rotatable connected with the second housing 300. The fastening member 500' has a connecting portion 510' and a connecting arm 520'. The connecting portion 510' has a screw hole 511' suitable for engaging with the screw 400, so that the connecting portion 510' can be driven by the screw 400 to move linearly on the screw 400 relative to the second housing 300.

In the present embodiment, the connecting arm 520' and the fastening portion 521' can be a generally V-shaped metallic spring plate. A portion of this generally V-shaped metallic spring plate is the connecting arm 520', and one end of the connecting arm 520' is inserted into the connecting portion 510. Another portion of this generally V-shaped metallic spring plate is the fastening portion 521'. The angle of the fastening portion 521' is designed to be suitable for passing the contact portion 210, and the shape of the fastening portion 521' is designed to co-operate with the fastening space 220 to lock the first housing 200 and the second housing 300. The movement of the fastening member 500' is similar to that of the fastening member 500 of the previous embodiment, therefore relevant descriptions are omitted here for concise purpose.

In the present embodiment, since the connecting arm 520' and the fastening portion 521' are made of metal, the locking mechanism can withstand larger torque after the fastening portion 521' enters into the fastening space 220.

Note that the shape of the fastening space 220 is not limited by those shown in the drawings, and can be adjusted according to practical needs (such as the change of the shape of the fastening portion 521 of the fastening member 500, or the change of the shape of the fastening portion 521' of the fastening member 500').

Figure 7A:
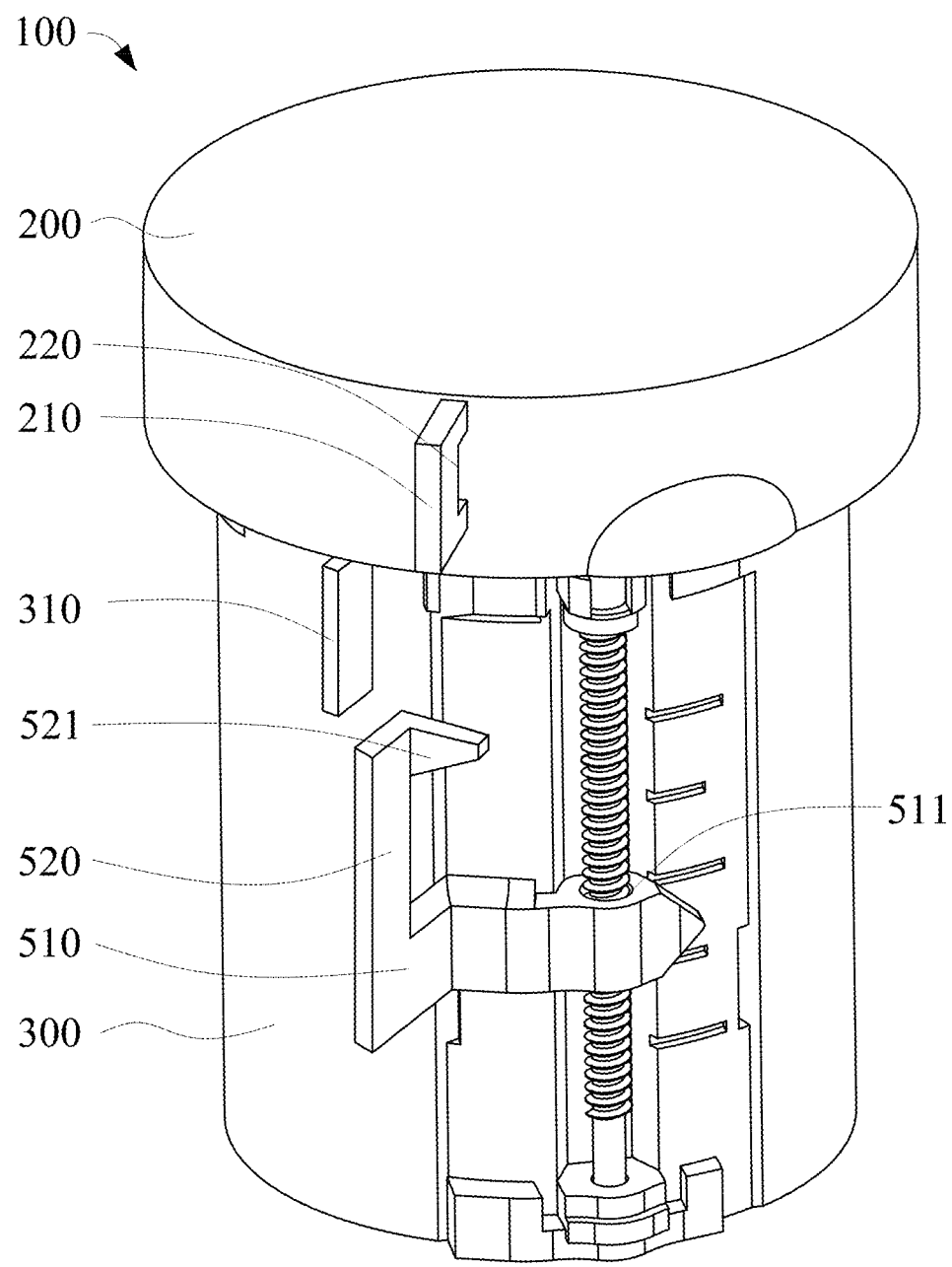
FIG. 7A is a schematic diagram showing another fastening space according to another embodiment of the invention.
Figure 7B:
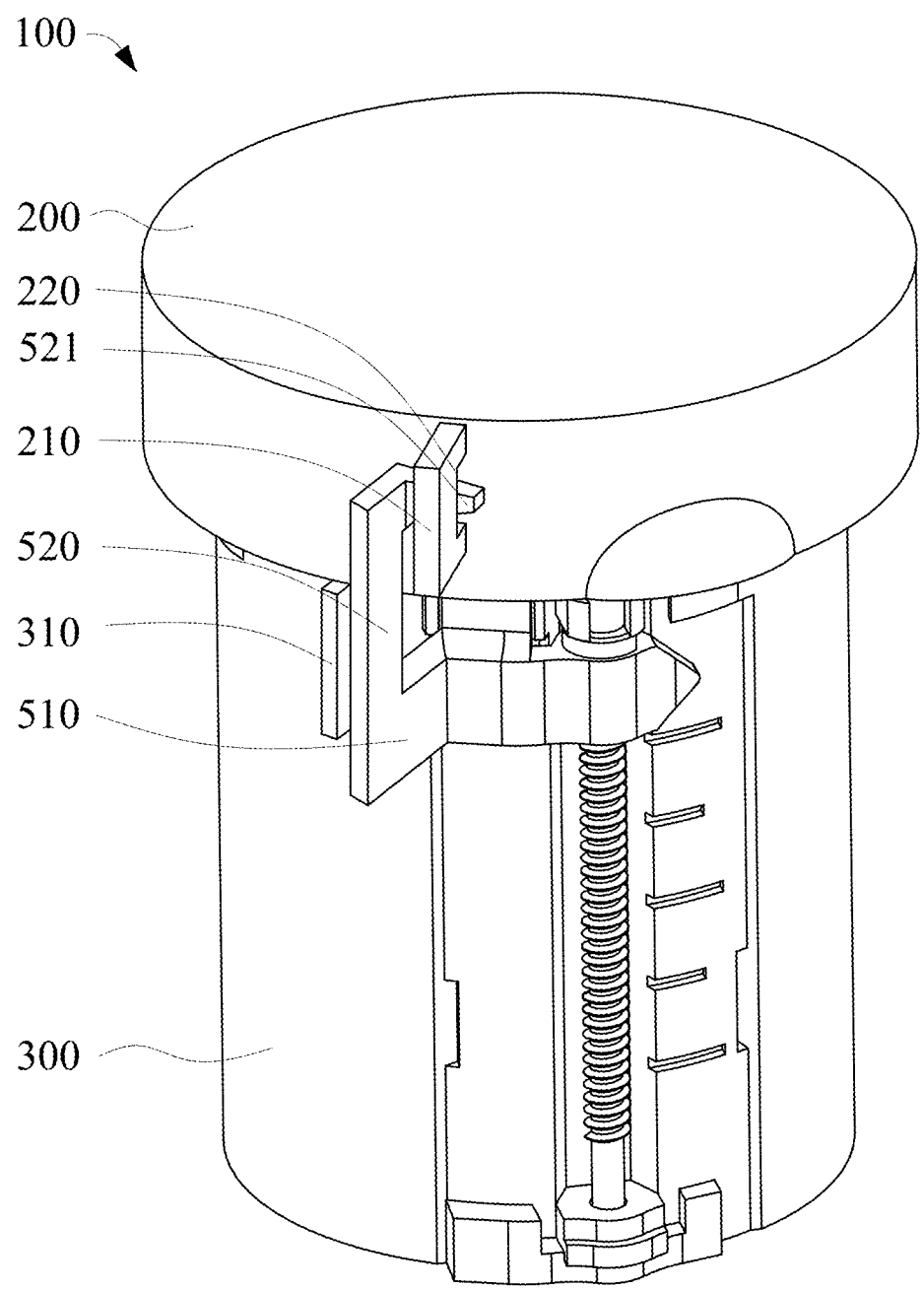
FIG. 7B is a schematic diagram showing the operation of the fastening space shown in FIG. 7A.

Referring to FIGS. 7A and 7B, except for the configuration mentioned above, the fastening space 220 may be a hole formed at the outside of the first housing 200, and the design of the connecting arm 520 and the fastening portion 521 of the fastening member 500 may be changed accordingly. To further limit the relative rotation between the first housing 200 and the second housing 300, a block 310 can be disposed at the outer surface 301 of the second housing 300. When the fastening space 220 limits the fastening portion 521, the fastening member 500 is limited between the block 310 and the fastening space 220 to prevent the fastening portion from falling off. The operations of the connecting arm 520 and the fastening portion 521 are similar to those described above with reference to FIGS. 5A to 5D, therefore relevant descriptions are omitted here for concise purpose.

In the present embodiment, under the initial state of the connecting arm 520 (or the connecting arm 520'), the distance between the fastening portion 521 (or the fastening portion 521') and the rotation axis A is larger than the distance between the outer surface 301 of the second housing 300 and the rotation axis A. Here, the distance between the fastening portion 521 (or the fastening portion 521') and the rotation axis A is defined as the average of the distances between each point on the fastening portion 521 (or the fastening portion 521') and the rotation axis A. In other words, the fastening member 500 and its fastening portion 521 are disposed independently outside the outer surface 301 of the second housing 300. Therefore, it is only necessary to provide the space for the connecting arm 520 to deform. It is not necessary to provide a space on the outer surface of the second housing 300 to accommodate the fastening member 500. Therefore, the structural complexity is reduced.

Moreover, compared to the conventional locking mechanism which needs to pre-press the fastening member, the fastening member 500 of the embodiment does not need to be pre-pressed, and therefore it is also not necessary to provide a portion to hold the pre-pressed fastening member. Therefore, the demolding difficulty can be prevented.

According to the locking mechanism for an aerosol drug delivery device disclosed herein, no pre-pressed fastening member is required. Therefore, the manufacturing costs and structural complexity are reduced, and issue of false locking can be solved.

While the present disclosure has been described by means of specific embodiments, numerous modifications and variations could be made thereto by those skilled in the art without departing from the scope and spirit of the present disclosure set forth in the claims.

What is claimed is:
1. A locking mechanism for an aerosol drug delivery device, comprising:
  a first housing having at least one contact portion and at least one fastening space formed beside the at least one contact portion;

a second housing rotatably connected with the first housing and being capable of rotating relative to the first housing along a rotation axis;

a screw rotatably connected with the second housing and being capable of rotating relative to the second housing along a central axis parallel to the rotation axis; and a fastening member movably and directly connected with the screw and capable of being driven by the screw to move toward the at least one contact portion, the fastening member including a fastening portion capable of being displaced when contacting with the at least one contact portion and entering into the at least one fastening space, the fastening portion is directly against the first housing to limit the relative rotation between the first housing and the second housing.

2. The locking mechanism according to claim 1, wherein under an initial state the fastening member is located at one end of the screw away from the first housing.

3. The locking mechanism according to claim 1, further comprising:

a projection disposed at the first housing, wherein the position of the projection corresponds to one end of the screw, and the projection contacts with the screw when the first housing rotates relative to the second housing to drive the screw to rotate along the central axis.

4. The locking mechanism according to claim 3, wherein the screw has a driven portion projected radially at the end contacting the projection for being driven by the projection.

5. The locking mechanism according to claim, 1, wherein the fastening member further includes:

a connecting portion having a screw hole for engaging with the screw; and a connecting arm having one end connected with the connection portion and another end being the fastening portion.

6. The locking mechanism according to claim 5, wherein the connecting portion and the connecting arm are integrally formed.

7. The locking mechanism according to claim 5, wherein the connecting arm is a metallic spring plate and is inserted into the connecting portion.

8. The locking mechanism according to claim 1, wherein the at least one fastening space is formed at an inner surface of the first housing.

9. The locking mechanism according to claim 1, wherein the at least one fastening space is formed at the outside of the first housing.

10. The locking mechanism according to claim 9, further comprising:

a block disposed at an outer surface of the second housing, wherein when the fastening portion is limited in the at least one fastening space, the fastening member is between the block and the at least one fastening space.

11. The locking mechanism according to claim 1, wherein when under an initial state, the distance between the fastening portion and the rotation axis is larger than the distance between an outer surface of the second housing and the rotation axis.

12. The locking mechanism according to claim 1, wherein the at least one fastening space is a fastening groove.

13. The locking mechanism according to claim 12, wherein a central angle between the two ends of the fastening groove is equal to or smaller than 25 degrees.

14. A method of using the locking mechanism for an aerosol drug delivery device, the aerosol drug delivery device including a first housing having at least one contact portion and at least one fastening space formed beside the at least one contact portion, a second housing rotatably connected with the first housing along a rotation axis, a screw rotatably connected with the second housing and being capable of rotating relative to the second housing along a central axis parallel to the rotation axis, and a fastening member movably and directly connected with the screw and capable of being driven by the screw to move toward the contact portion, the fastening member including a fastening portion, the method comprising the steps of:

rotating the second housing relative to the first housing to rotate the screw along the central axis to drive the fastening member to move toward the at least one contact portion; and further rotating the second housing relative to the first housing to make the fastening portion be displaced when contacting with the at least one contact portion and then enter into the at least one fastening space and making the fastening portion directly against the first housing to limit the relative rotation between the first housing and the second housing.

15. The method according to claim 14, wherein in the first rotating step the fastening member is moved from an initial state located at one end of the screw away from the first housing.

16. The method according to claim 15, wherein in the second rotating step the fastening portion restored to enter into the at least one fastening space after being displaced by the at least one contact portion.

* * * * *